United States Patent
Kim et al.

(10) Patent No.: US 11,129,741 B2
(45) Date of Patent: Sep. 28, 2021

(54) PASSIVE ANKLE ASSIST APPARATUS WITH TORSIONAL COIL SPRING

(71) Applicant: Agency for Defense Development, Daejeon (KR)

(72) Inventors: Gwang Tae Kim, Daejeon (KR); Tae Woo Park, Daejeon (KR); Young June Shin, Daejeon (KR); Man Bok Hong, Daejeon (KR); Young Cheol Kim, Daejeon (KR); Byoung Ju Lee, Daejeon (KR)

(73) Assignee: Agency for Defense Development, Daejeon (KR)

( * ) Notice: Subject to any disclaimer, the term of this patent is extended or adjusted under 35 U.S.C. 154(b) by 0 days.

(21) Appl. No.: 17/122,150

(22) Filed: Dec. 15, 2020

(65) Prior Publication Data
US 2021/0259872 A1 Aug. 26, 2021

(30) Foreign Application Priority Data

Feb. 26, 2020 (KR) .................. 10-2020-0023731

(51) Int. Cl.
*A61F 5/01* (2006.01)
*A61H 3/00* (2006.01)
*A61H 1/02* (2006.01)

(52) U.S. Cl.
CPC ......... *A61F 5/0127* (2013.01); *A61H 1/0266* (2013.01); *A61H 3/00* (2013.01);
(Continued)

(58) Field of Classification Search
CPC ............ A61F 5/0127; A61F 2005/0179; A61F 2005/0169; A61F 2005/0197; A61H 1/0266; A61H 3/00; A61H 2201/165; A61H 2201/1676; A61H 2201/1253; A61H 2201/1269; A61H 2201/164; A61H 2201/1671; A61H 2201/1642;
(Continued)

(56) References Cited

U.S. PATENT DOCUMENTS 2,439,100 A * 4/1948 Richards ............... A61F 5/0127
602/28
2,440,894 A * 5/1948 Caesar ................. A61H 1/0266
602/29
(Continued)

FOREIGN PATENT DOCUMENTS

JP 2004-166811 A 6/2004
KR 101682450 B1 12/2016
KR 10-2019-0036748 A 4/2019

*Primary Examiner* — Justine R Ryu
*Assistant Examiner* — Kelsey E Baller
(74) *Attorney, Agent, or Firm* — Mintz Levin Cohn Ferris Glovsky and Popeo, P.C.

(57) ABSTRACT

A passive ankle assist apparatus with a torsional coil spring for assisting an ankle joint of a user in a state of being mounted on a shoe worn by the user includes a shank frame mountable on a shank of the user, the shank frame including a guide hole, a torsional coil spring including a coil part provided in a state of being wound around a central portion a plurality of times, the torsional coil spring slidable along the guide hole, a support part configured to support the coil part, and a coupling frame configured to support the support part, the coupling frame couplable to the shoe.

7 Claims, 7 Drawing Sheets

(52) U.S. Cl.
CPC .......................... *A61F 2005/0179* (2013.01); *A61H 2201/165* (2013.01); *A61H 2201/1642* (2013.01); *A61H 2201/1671* (2013.01); *A61H 2201/1676* (2013.01)

(58) Field of Classification Search
CPC .......... A61H 2003/007; A61H 2205/10; A61H 2205/106; A61H 2205/12; B25J 9/0006; B25J 9/16
USPC .......... 602/5, 23, 27–29, 62, 65; 601/23–28, 601/33–35
See application file for complete search history.

(56) References Cited

U.S. PATENT DOCUMENTS

| | | | | |
|---|---|---|---|---|
| 2,567,195 | A * | 9/1951 | Ellery ................... | A61F 5/0127 602/28 |
| 3,086,521 | A * | 4/1963 | Desai .................... | A61F 5/0127 602/16 |
| 3,589,359 | A * | 6/1971 | Hill .......................... | A43B 7/20 602/28 |
| 3,732,861 | A * | 5/1973 | Lehneis ................ | A61F 5/0127 602/16 |
| 3,859,991 | A * | 1/1975 | Theodores ............ | A61F 5/0113 602/28 |
| 4,397,308 | A * | 8/1983 | Hepburn ............... | A61F 5/0102 602/16 |
| 4,459,980 | A * | 7/1984 | Perser ................... | A61F 5/0113 128/DIG. 15 |
| 2008/0300525 | A1 * | 12/2008 | Shlomovitz ........... | A61F 5/0111 602/28 |
| 2009/0227928 | A1 * | 9/2009 | Drake ................... | A61F 5/0113 602/28 |
| 2018/0318122 | A1 * | 11/2018 | LeCursi ................ | B29C 64/386 |

\* cited by examiner

PASSIVE ANKLE ASSIST APPARATUS WITH TORSIONAL COIL SPRING

CROSS-REFERENCE TO RELATED APPLICATION(S)

This application claims the benefit of Korean Patent Application No. 10-2020-0023731, filed on Feb. 26, 2020, in the Korean Intellectual Property Office, the disclosure of which is incorporated herein by reference.

BACKGROUND

1. Field of the Invention

Example embodiments relate to a passive ankle assist apparatus using a torsional coil spring.

2. Description of the Related Art

An exoskeleton apparatus, which is an apparatus worn by a person, is a system that assists and supports muscular strength of a body part of a wearer. The exoskeleton apparatus may be classified into an active-type exoskeleton apparatus and a passive-type exoskeleton apparatus depending on the presence or absence of a power source, and may be classified into a whole body-type exoskeleton apparatus, an upper limb-type exoskeleton apparatus, and a lower limb-type exoskeleton apparatus or an articulated exoskeleton apparatus depending on a body part where muscular strength support is required.

Ankle assist exoskeleton apparatuses have been mostly developed to assist walking or running since it is easy to apply a passive mechanism in view of motion characteristics of an ankle, a passive exoskeleton to which a wire and a clutch are applied has been developed. However, conventional passive ankle assist exoskeleton apparatuses mostly include an ankle joint of a single pin joint and a footrest formed of a hard material to restrict a degree of freedom of a foot and an ankle, resulting in discomfort upon wearing. In addition, a shear force generated in a fastening portion of a human body due to a discrepancy in center between the joint and the ankle joint of the exoskeleton apparatus also causes the wearer's discomfort.

SUMMARY

An aspect provides a passive ankle assist apparatus with a torsional coil spring for addressing the issue of causing discomfort upon wearing by restraining a degree of freedom of a foot and an ankle, and the issue in which a shear force generated in a fastening portion due to a discrepancy in center between a joint and an ankle joint of an exoskeleton apparatus causes the wearer's discomfort.

Specifically, a passive ankle assist apparatus having a torsional coil spring according to an aspect aims to propose a passive ankle assist mechanism capable of reducing the shear force transmitted to a human body without restricting the degree of freedom of the foot and ankle.

According to an aspect, there is provided a passive ankle assist apparatus with a torsional coil spring, the passive ankle assist apparatus with a torsional coil spring for assisting an ankle joint of a user in a state of being mounted on a shoe worn by the user, including a shank frame mountable on a shank of the user, the shank frame including a guide hole, a torsional coil spring including a coil part provided in a state of being wound around a central portion a plurality of times, the torsional coil spring slidable along the guide hole, a support part configured to support the coil part, and a coupling frame configured to support the support part, the coupling frame couplable to the shoe.

The torsional coil spring may further include an engaging part formed to extend downward from the coil part, the engaging part engageable with the coupling frame based on an angle formed by the shank frame and the coupling frame, and a sliding part formed to extend upward from the coil part, the sliding part slidable along the guide hole.

The coupling frame may include a frame hole configured to receive the engaging part, and the engaging part may include an extension rod formed to extend in parallel with an outer surface of the coupling frame, and an engaging rod bent and formed to extend from one end of the extension rod, the engaging rod configured to pass through the frame hole.

The engaging part may further include a separation prevention rod bent and formed to extend from one end of the engaging rod, the separation prevention rod formed to extend in parallel with an inner surface of the coupling frame.

The separation prevention rod may be parallel with the extension rod.

An angle formed by the engaging part and the sliding part may be changeable in a state in which the engaging part is engaged with the coupling frame.

Elastic energy stored in the coil part may change while the angle formed by the engaging part and the sliding part changes.

The sliding part may include a vertical rod formed to extend upward from the coil part, a horizontal rod bent and formed to extend from one end of the vertical rod, and a sliding rod bent and formed to extend from one end of the horizontal rod, the sliding rod slidable with respect to the shank frame in a state of being received inside the guide hole.

The support part may be adjustable in position with respect to the coupling frame.

The passive ankle assist apparatus with a torsional coil spring may further include a coupling part formed to protrude from an inner surface of the coupling frame.

According to another aspect, there is provided a passive ankle assist apparatus with a torsional coil spring including a shank frame including a first guide hole and a second guide hole formed in parallel with each other, the shank frame mountable on a shank of a user, a first torsional coil spring including a first coil part provided in a state of being wound around a central portion a plurality of times, the first torsional coil spring slidable along the first guide hole, a second torsional coil spring including a second coil part provided in a state of being wound around the central portion a plurality of times, the second torsional coil spring slidable along the second guide hole, a first support part configured to support the first coil part, a second support part configured to support the second coil part, a first coupling frame configured to support the first support part, and a second coupling frame configured to support the second support part, the second coupling frame facing the first coupling frame.

The passive ankle assist apparatus with a torsional coil spring may further include a support band configured to surround a shank and a calf of the user, the support band connected to the shank frame.

The first torsional coil spring and the second torsional coil spring may be each independently slidable relatively with respect to the shank frame.

The first coupling frame and the second coupling frame may be spaced apart from each other without being directly connected to each other.

The first torsional coil spring and the second torsional coil spring may each include an engaging part formed to extend downward from the coil part, the engaging part engageable with the coupling frame based on an angle formed by the shank frame and the coupling frame, and a sliding part formed to extend upward from the coil part, the sliding part slidable along the guide hole.

According to still another aspect, there is provided a passive ankle assist apparatus with a torsional coil spring, the passive ankle assist apparatus with a torsional coil spring for assisting an ankle joint of a user in a state of being mounted on a shoe worn by the user, including a shank frame including a first guide hole and a second guide hole formed in parallel with each other, the shank frame mountable on a shank of the user, a first torsional coil spring including a first coil part provided in a state of being wound around a central portion a plurality of times, the first torsional coil spring slidable along the first guide hole, a second torsional coil spring including a second coil part provided in a state of being wound around the central portion a plurality of times, the second torsional coil spring slidable along the second guide hole, a first support part configured to support the first coil part, a second support part configured to support the second coil part, a first coupling frame configured to support the first support part, the first coupling frame mountable on an outside of the shoe, and a second coupling frame configured to support the second support part, the second coupling frame facing the first coupling frame, and mountable on an inside of the shoe.

Additional aspects of example embodiments will be set forth in part in the description which follows and, in part, will be apparent from the description, or may be learned by practice of the disclosure.

A passive ankle assist apparatus with a torsional coil spring according to an example embodiment may have a technical effect of reducing a load of an ankle joint while reducing muscle fatigue of gastrocnemius and soleus muscles of a wearer during walking.

In addition, the passive ankle assist apparatus with a torsional coil spring according to an example embodiment may not have a hard footrest and may not restrict a degree of freedom of the ankle joint, thereby preventing various muscles surrounding an ankle and a foot from tensing unnecessarily for position stabilization.

In addition, the passive ankle assist apparatus with a torsional coil spring according to an example embodiment may have a coupling frame and a torsional coil spring respectively arranged in an inside and an outside thereof per foot, and accordingly may have a technical effect of allowing both an inside and an outside of a foot to independently adjust a position of a center of rotation and adjust rigidity of a spring. Thus, a center of rotation of the ankle that is not perpendicular to a sagittal plane may correspond to a center of pressure that follows the outside of the foot during stance.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Hereinafter, example embodiments will be described in detail with reference to the accompanying drawings. Regarding the reference numerals assigned to the components in the drawings, it should be noted that the same components will be designated by the same reference numerals, wherever possible, even though they are shown in different drawings. Also, in the description of example embodiments, detailed description of well-known related structures or functions will be omitted when it is deemed that such description will cause ambiguous interpretation of the example embodiments.

In addition, terms such as first, second, A, B, (a), (b), and the like may be used herein to describe components of the example embodiments. These terms are only used to distinguish one component from another component, and essential, order, or sequence of corresponding components are not limited by these terms. It will be understood that when one component is referred to as being "connected to", "coupled to", or "linked to" another component, one component may be "connected to", "coupled to", or "linked to" another component via a further component although one component may be directly connected to or directly linked to another component.

The same name may be used to describe a component included in an example embodiment and a component having a common function in another example embodiment. Unless otherwise mentioned, the description on the example embodiment may be applicable to the other example embodiment and thus, duplicated description will be omitted for conciseness.

Figure 1:
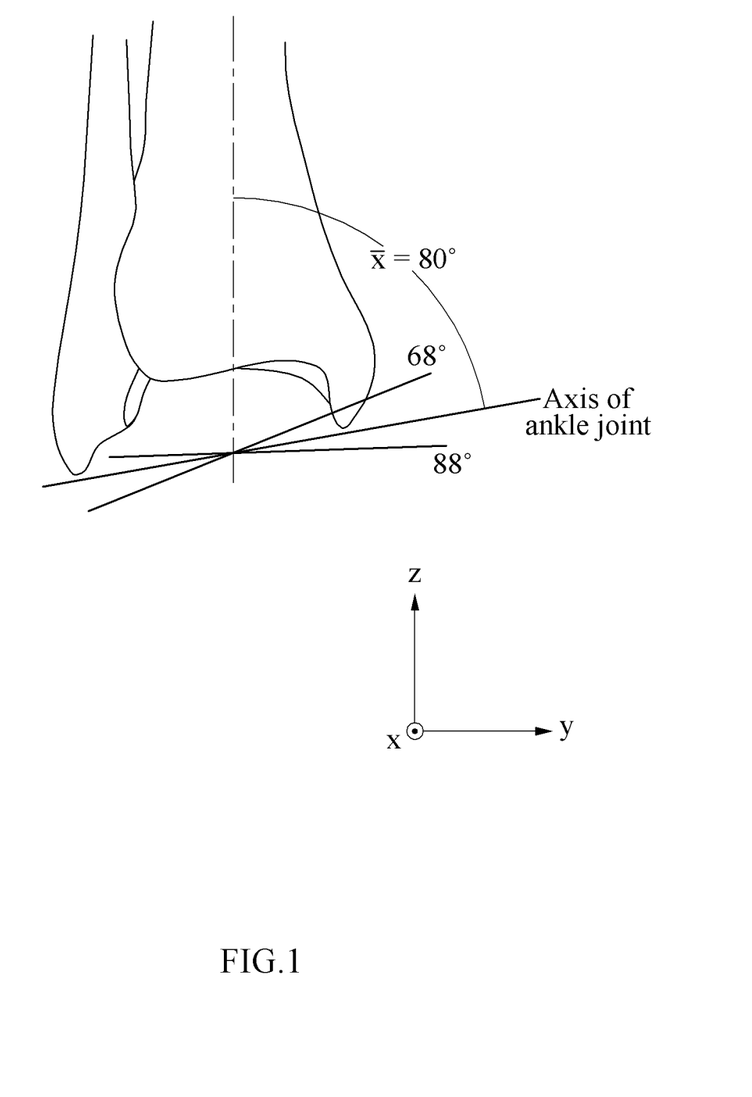
FIGS. 1 and 2 are schematic views illustrating an ankle joint that is not perpendicular to a sagittal plane according to an example embodiment.
Figure 2:
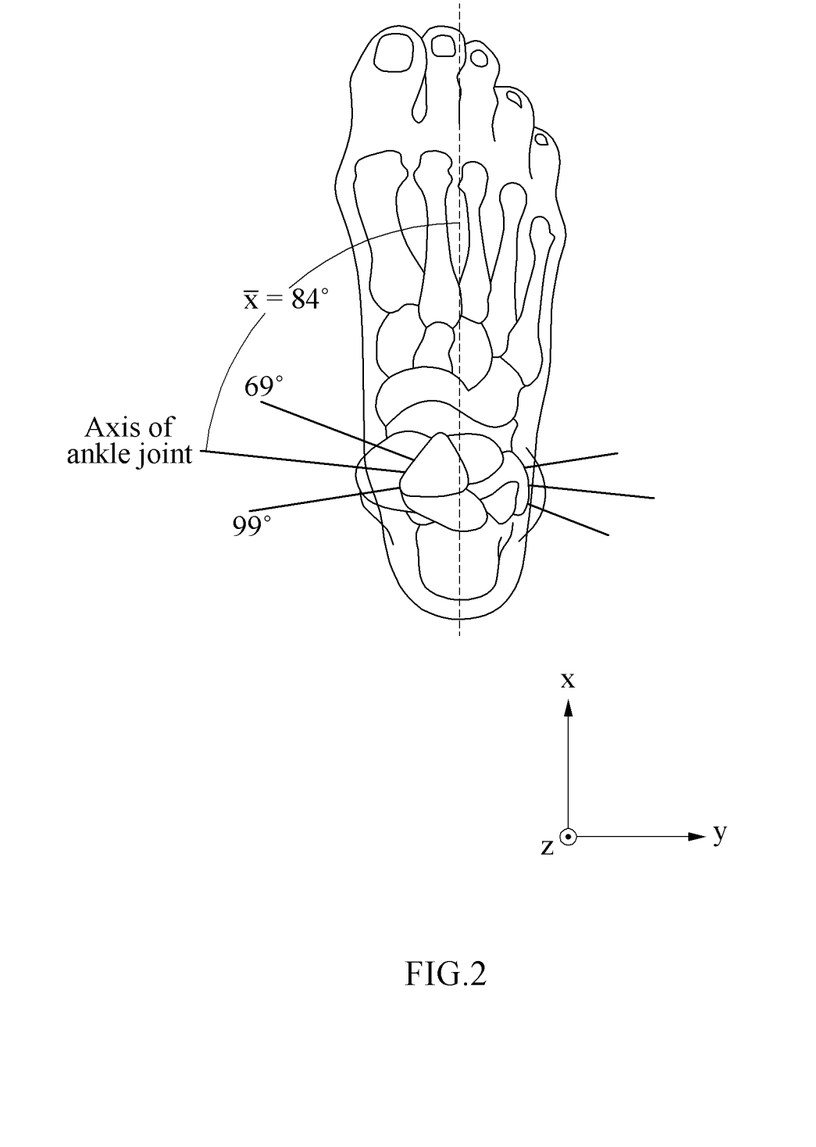

FIGS. 1 and 2 are schematic views illustrating an ankle joint that is not perpendicular to a sagittal plane according to an example embodiment.

Referring to FIGS. 1 and 2, a center of rotation of the ankle joint may not be perpendicular to the sagittal plane. Specifically, on the basis of coordinate axes illustrated in FIGS. 1 and 2, it can be seen that a rotation axis of an ankle is formed at an angle of about 68 to 88 degrees with respect to a z-axis even on a y-z plane, in other words, is not parallel with a y-axis, and is not generally parallel with the y-axis in a state of being formed at an angle of about 69 to 99 degrees with respect to an x-axis even on an x-y plane. It can be seen that the angle of the rotation axis of the ankle joint may be slightly different for each person, but in general, the angle of the rotation axis of the ankle joint is not perpendicular to the sagittal plane.

The passive ankle assist apparatus with a torsional coil spring according to an example embodiment described in detail below may provide a mechanism capable of effectively assisting the ankle joint without restricting a degree of freedom of the ankle joint.

Figure 3:
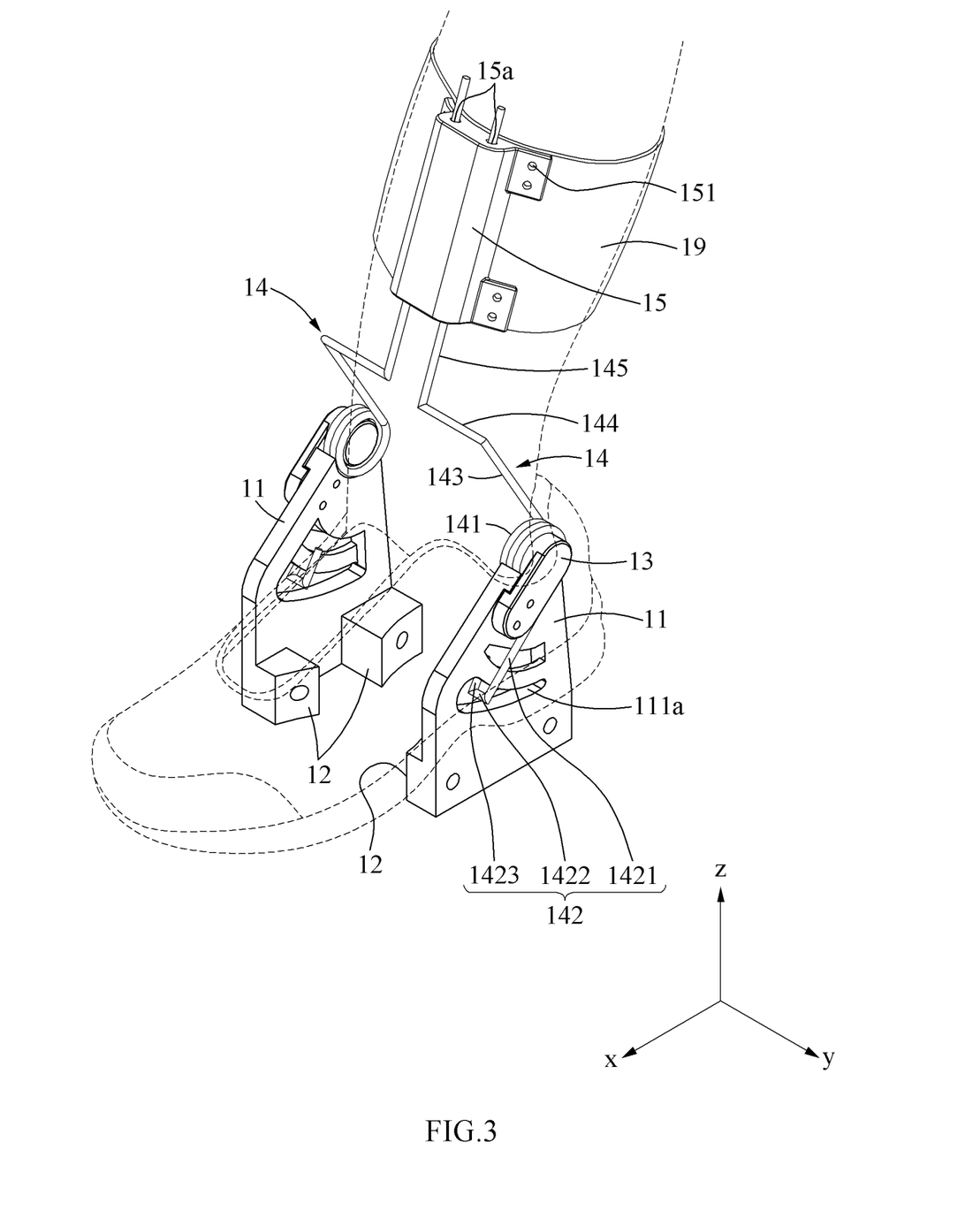
FIG. 3 is a perspective view illustrating a passive ankle assist apparatus with a torsional coil spring according to an example embodiment.

FIG. 3 is a perspective view illustrating a passive ankle assist apparatus with a torsional coil spring according to an example embodiment.

Figure 4:
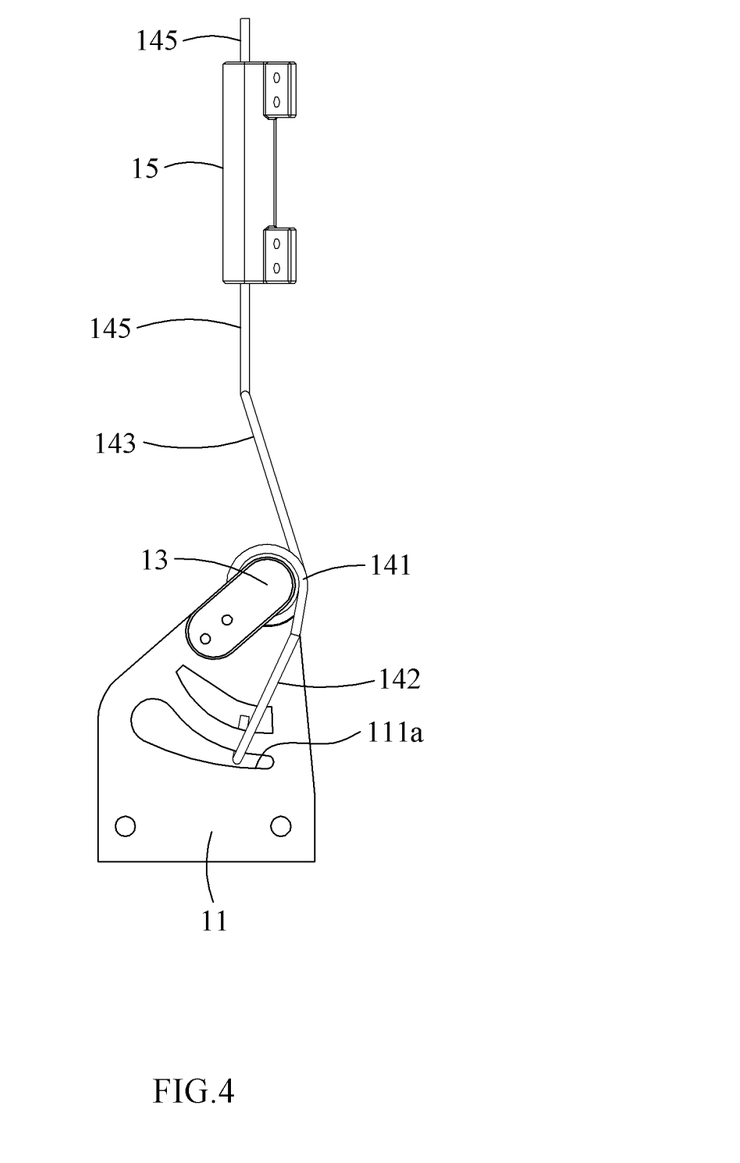
FIG. 4 is a side view illustrating a passive ankle assist apparatus with a torsional coil spring that is in an initial state according to an example embodiment.
Figure 5:
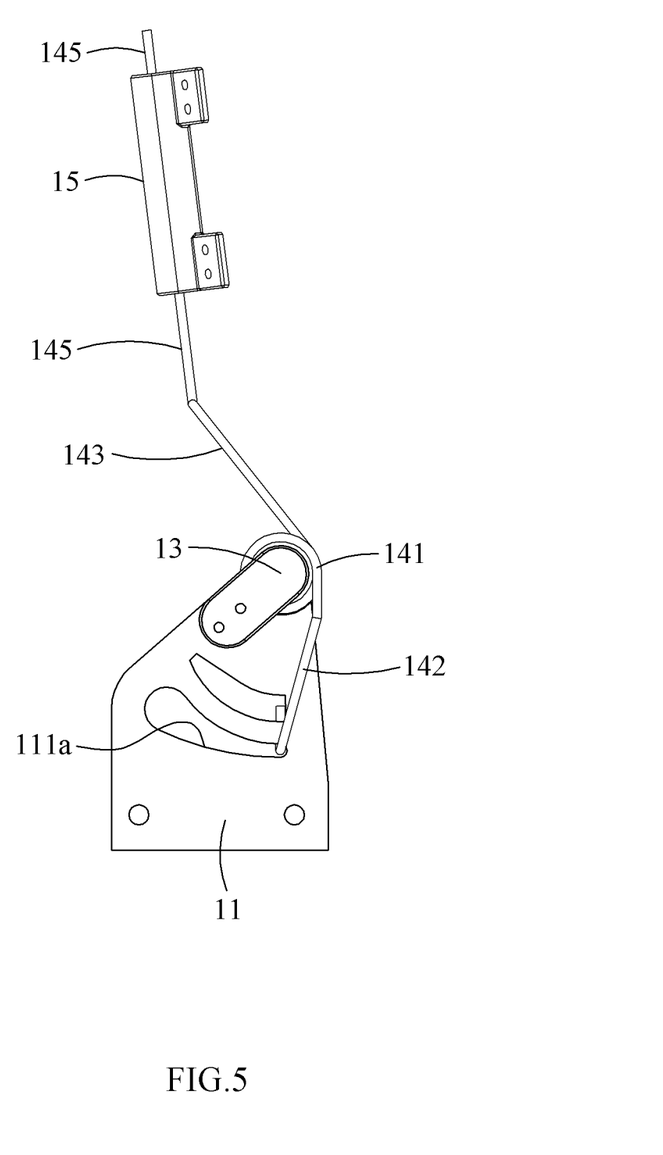
FIG. 5 is a side view illustrating a passive ankle assist apparatus with a torsional coil spring that assists a toe-off operation according to an example embodiment.
Figure 6:
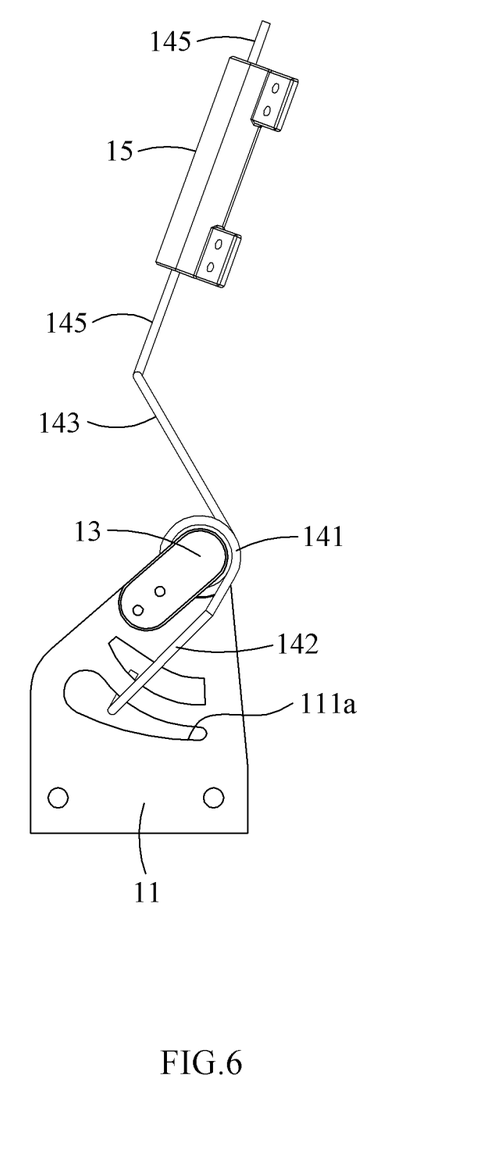
FIG. 6 is a side view illustrating a passive ankle assist apparatus with a torsional coil spring that is in a swing phase of a gait cycle according to an example embodiment.

FIG. 4 is a side view illustrating a passive ankle assist apparatus with a torsional coil spring that is in an initial state according to an example embodiment, FIG. 5 is a side view illustrating a passive ankle assist apparatus with a torsional coil spring that assists a toe-off operation according to an example embodiment, and FIG. 6 is a side view illustrating a passive ankle assist apparatus with a torsional coil spring that is in a swing phase of a gait cycle according to an example embodiment.

Figure 7:
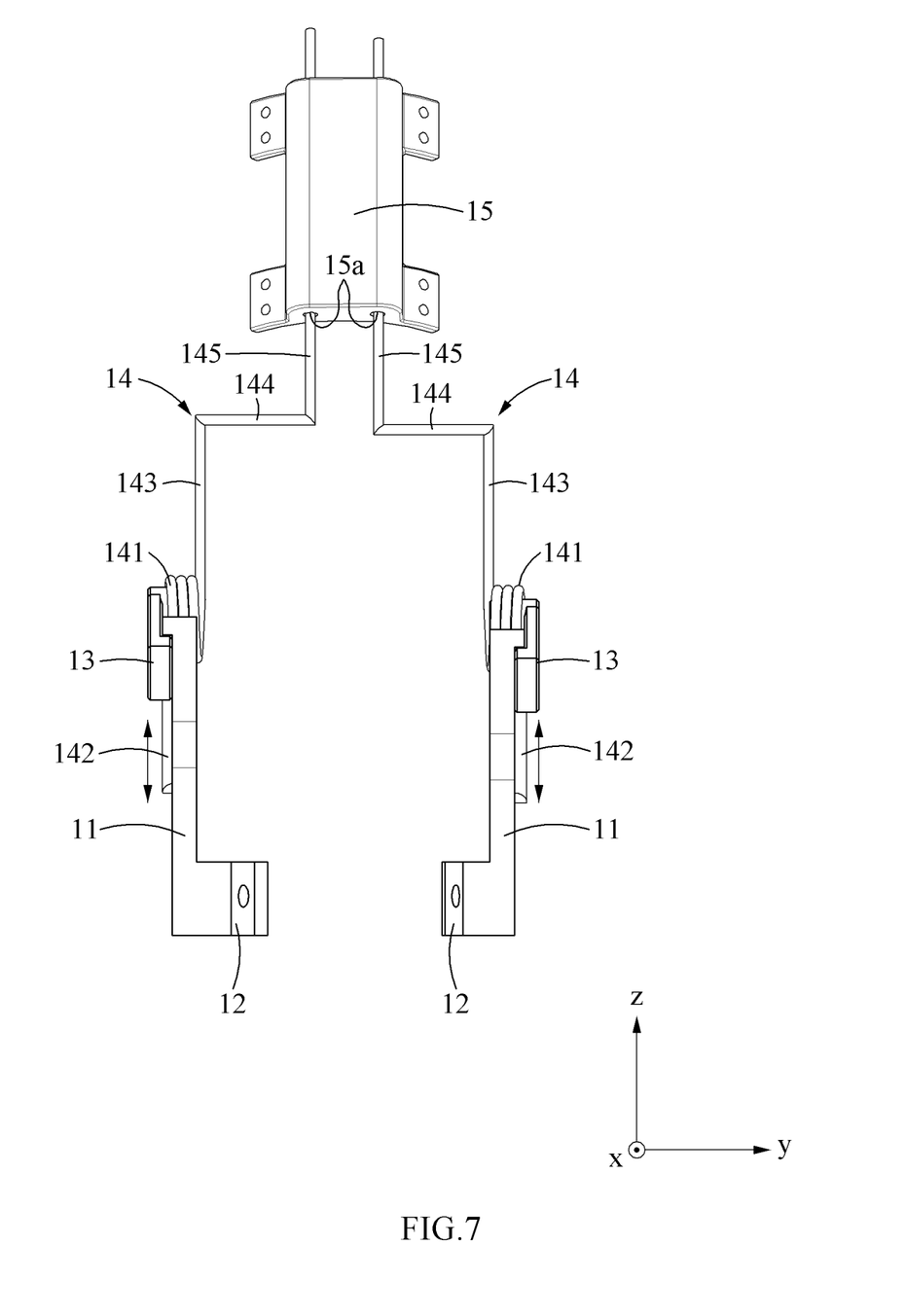
FIG. 7 is a front view illustrating a passive ankle assist apparatus with a torsional coil spring according to an example embodiment.

FIG. 7 is a front view illustrating a passive ankle assist apparatus with a torsional coil spring according to an example embodiment.

Referring to FIGS. 3 to 7, the passive ankle assist apparatus having a torsional coil spring (hereinafter referred to as an ankle assist apparatus) according to an example embodiment may not restrict a degree of freedom of an ankle joint of a user, and also may effectively assist movement of the ankle joint. In addition, the ankle assist apparatus according to an example embodiment may be manufactured to be lightweight.

The ankle assist apparatus may assist the user's ankle joint in a state of being mounted on a shoe worn by the user. The ankle assist apparatus may include a coupling frame 11, a coupling part 12, a support part 13, a torsional coil spring 14, a shank frame 15, and a support band 19. The torsional coil spring 14 may connect the coupling frame 11 and the shank frame 15 to each other, and may be elastically deformed in accordance with an angle between the coupling frame 11 and the shank frame 15, thereby storing elastic energy and assisting the user's walking through a restoring force. Specifically, the ankle assist apparatus may assist a toe-off phase and/or a push-off phase during a gait cycle of the user.

Two coupling frames 11, two coupling parts 12, two support parts 13, and two torsional coil springs 14 may be provided. The coupling frame 11 and the coupling part 12 may respectively include a first coupling frame and a first coupling part coupled to an outside (+y direction) of the shoe, and a second coupling frame and a second coupling part coupled to an inside (−y direction) of the shoe. In addition, the support part 13 and the torsional coil spring 14 may respectively include a first support part and a first torsional coil spring provided on the outside (+y direction) with respect to a foot of the user, and a second support part and a second torsional coil spring provided on the inside (−y direction) with respect to the foot of the user. For ease of description, it is should be noted that reference numerals of a first configuration are not distinguished from those of a second configuration.

The coupling frame 11 may support the support part 13, and may be mountable on the shoe. The coupling frame 11 may be mounted on the shoe through the coupling part 12. The coupling frame 11 may partially cover an outer surface of the shoe. The first coupling frame 11 may cover the outer surface of the shoe, and the second coupling frame 11 may cover an inner surface of the shoe. The first coupling frame and the second coupling frame may face each other in a state of being spaced apart from each other without being directly connected to each other. The coupling frame 11 may be provided with a frame hole 111a configured to receive a part of the torsional coil spring 14. The coupling frame 11 may be provided with a hole structure for weight reduction in addition to the frame hole 111a3. The frame hole 111a may have an approximately arc shape based on the coil part 141.

The coupling part 12 may be formed to protrude from an inner surface of the coupling frame 11, and may be couplable to the shoe. The first coupling part 12 may be formed to protrude from an inner surface (a surface facing the −y direction) of the first coupling frame 11. The second coupling part 12 may be formed to protrude from an inner surface (+y direction) of the second coupling frame 11. It should be noted that the coupling part 12 is illustrated in the drawings as being coupled to a side portion of the shoe, but is not limited thereto. For example, the coupling part 12 may be coupled to the side portion of the shoe, or may be coupled to a bottom portion of the shoe. The first coupling part and the second coupling part may each independently function without being connected to each other. For example, a change in a position of the first coupling part may not affect a change in a position of the second coupling part.

The support part 13 may support the torsional coil spring 14. For example, the support part 13 may support the coil part 141 of the torsional coil spring 14. The support part 13 may be mounted on the coupling frame 11. A position where the support part 13 is mounted on the coupling frame 11 may be adjustable. For example, a plurality of screw holes may be provided on the support part 13, and the user may adjust a position of the support part in a manner of selecting a screw hole fixed to the coupling frame 11 from among the plurality of screw holes provided on the support part 13. By adjusting the position of the support part 13, the coil part 141 of the torsional coil spring 14 may be adjusted to be positioned in the vicinity of a rotation axis of the ankle joint. In addition, the user may independently adjust positions of the first support part and the second support part. For example, with respect to the rotation axis of the ankle joint, an outer portion of the rotation axis may be positioned above an inner portion of the rotation axis, as illustrated in FIG. 1. In this case, by setting the first support part to be positioned relatively above the second support part, each of the first support part and the second support part may be set to be parallel with the rotation axis of the ankle joint of the user.

The torsional coil spring 14 may include the coil part 141 that is provided in a state of being wound around a central portion a plurality of times, an engaging part 142 that is formed to protrude downward from the coil part 141, and is engageable with the coupling frame 11 based on an angle formed by the shank frame 15 and the coupling frame 11, and sliding parts 143, 144, and 145 that are formed to extend upward from the coil part 141, and are slidable along a guide hole.

The coil part 141 may store elastic energy through elastic deformation, and may generate a restoring force through the stored elastic energy to assist the user's walking. For example, the coil part 141 may support the toe-off operation in a manner of contracting from a certain point of a latter half process from a heel-strike phase to the toe-off phase, and expanding in the toe-off phase.

The torsional coil spring 14 may be slidable with respect to the shank frame 15. Through such a structure, the user may perform an eversion operation and/or an inversion operation of the ankle joint, or the user may perform a supination operation and/or a pronation operation of the ankle joint. That is, the torsional coil spring 14 may guarantee a degree of freedom of the ankle joint of the user through a mechanism of sliding along the shank frame 15.

The engaging part 142 may include an extension rod 1421 that is formed to extend in parallel with an outer surface of the coupling frame 11, an engaging rod 1422 that is bent and formed to extend from one end of the extension rod 1421, and passes through the frame hole 111a, and a separation prevention rod 1423 that is bent and formed to extend from one end of the engaging rod 1422, and is formed to extend in parallel with the inner surface of the coupling frame 11. For example, the separation prevention rod 1423 may be parallel with the extension rod 1421. The separation preventing rod 1423 may allow the engaging part 142 to have a structure of surrounding the coupling frame 11, thereby preventing the engaging part 142 from being separated to the outside of the coupling frame 11.

The torsional coil spring 14 may be rotatable around the support part 13. For example, the torsional coil spring 14 may rotate clockwise or counterclockwise around the support part 13 based on an angle formed by the foot and shank of the user. For example, briefly giving a description based on the first torsional coil spring mounted on the outside of the shoe, while the user proceeds from the heel-strike phase to the toe-off phase, the engaging part 142 of the torsional coil spring 14 may be engaged with the coupling frame 11. In a state in which the engaging part 142 is engaged with the coupling frame 11, an angle formed by the engaging part 142 and the sliding parts 143, 144, and 145 may be changeable. While the angle formed by the engaging part 142 and the sliding parts 143, 144, and 145 changes, elastic energy stored in the coil part 141 may change. When proceeding to the toe-off phase in a state in which the engaging part 142 is engaged with the coupling frame 11, the sliding parts 143, 144, and 145 may further rotate counterclockwise around a y-axis in a state in which the engaging part 142 is fixed, and the coil part 141 may contract. As the coil part 141 contracts, the stored elastic energy may be used to assist the user's toe-off.

The sliding parts 143, 144, and 145 may include a vertical rod 143 that is formed to extend upward from the coil part 141, a horizontal rod 144 that is bent and formed to extend from one end of the vertical rod 143, and a sliding rod 142 that is bent and formed to extend from one end of the horizontal rod 144, and is slidable with respect to the shank frame 15 in a state of being received inside the guide hole of the shank frame 15. Through such a structure, the shank frame 15 may be provided in front of the user's shank, and the coupling frame 11 may cover the side portion of the shoe, and the torsional coil spring 14 may connect the shank frame 15 and the coupling frame 11 provided at different angles in this way to each other.

The shank frame 15 may be mountable on the user's shank, and may include the guide hole. The guide hole may receive a part of the torsional coil spring 14. The guide hole may guide the torsional coil spring so as to be slidable with one degree of freedom.

The support band 19 may surround the user's shank and calf, and may be connected to the shank frame 15. For example, the support band 19 may have elasticity. The shank frame 15 may be provided with a fixing hole 151 for fixation to the support band 19.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

What is claimed is:

1. A passive ankle assist apparatus with a torsional coil spring, the passive ankle assist apparatus with a torsional coil spring for assisting an ankle joint of a user in a state of being mounted on a shoe worn by the user, comprising:
    a shank frame mountable on a shank of the user, the shank frame comprising a guide hole;
    the torsional coil spring comprising a coil part provided in a state of being wound around a central portion a plurality of times, the torsional coil spring slidable along the guide hole;
    a support part configured to support the coil part;
    a coupling frame configured to support the support part, the coupling frame couplable to the shoe;
    an engaging part formed to extend downward from the coil part, the engaging part engageable with the coupling frame based on an angle formed by the shank frame and the coupling frame; and
    a sliding part formed to extend upward from the coil part, the sliding part slidable along the guide hole,
    wherein
    the coupling frame comprises a frame hole configured to receive the engaging part, and
    the engaging part comprises:
    an extension rod formed to extend in parallel with an outer surface of the coupling frame; and
    an engaging rod bent and formed to extend from one end of the extension rod, the engaging rod configured to pass through the frame hole.

2. The passive ankle assist apparatus with the torsional coil spring of claim 1, wherein the engaging part further comprises:
    a separation prevention rod bent and formed to extend from one end of the engaging rod, the separation prevention rod formed to extend in parallel with an inner surface of the coupling frame.

3. The passive ankle assist apparatus with the torsional coil spring of claim 2, wherein the separation prevention rod is parallel with the extension rod.

4. The passive ankle assist apparatus with the torsional coil spring of claim 3, wherein elastic energy stored in the coil part changes while the angle formed by the engaging part and the sliding part changes.

5. The passive ankle assist apparatus with torsional coil spring of claim 1, wherein the sliding part comprises:
    a vertical rod formed to extend upward from the coil part;
    a horizontal rod bent and formed to extend from one end of the vertical rod; and
    a sliding rod bent and formed to extend from one end of the horizontal rod, the sliding rod slidable with respect to the shank frame in a state of being received inside the guide hole.

6. The passive ankle assist apparatus with torsional coil spring of claim 1, wherein the support part is adjustable in position with respect to the coupling frame.

7. The passive ankle assist apparatus with torsional coil spring of claim 1, further comprising:
    a coupling part formed to protrude from an inner surface of the coupling frame.

* * * * *